United States Patent
Stevanovic et al.

(10) Patent No.: US 10,782,232 B2
(45) Date of Patent: Sep. 22, 2020

(54) QUALITY CONTROL MATERIAL, SYSTEM AND METHOD

(71) Applicant: Roche Diagnostics Operations, Inc., Indianapolis, IN (US)

(72) Inventors: Sabrina Stevanovic, Lenzburg (CH); Rebecca Ravotti, Vicoforte (IT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 208 days.

(21) Appl. No.: 15/710,950

(22) Filed: Sep. 21, 2017

(65) Prior Publication Data
US 2018/0095036 A1    Apr. 5, 2018

(30) Foreign Application Priority Data
Sep. 30, 2016   (EP) ..................................... 16191700

(51) Int. Cl.
*G01N 33/72* (2006.01)
*G01N 35/00* (2006.01)
(Continued)

(52) U.S. Cl.
CPC ... *G01N 21/4785* (2013.01); *G01N 33/54393* (2013.01); *G01N 33/72* (2013.01);
(Continued)

(58) Field of Classification Search
CPC ......... G01N 21/4785; G01N 33/54393; G01N 33/72; G01N 33/96; G01N 33/721; G01N 2496/15; G01N 35/00
See application file for complete search history.

(56) References Cited

U.S. PATENT DOCUMENTS 6,174,728 B1   1/2001  Ben-David et al.
9,361,561 B2 * 6/2016  Bown ................ G01N 21/8806
(Continued)

OTHER PUBLICATIONS

Ali, Yadollahpour et al., Dye-Doped Fluorescent Nanoparticles in Molecular Imaging: A Review of Recent Advances and Future Opportunities, Material Science Research India, 2014, pp. 102-113, vol. 11, No. 2.
(Continued)

*Primary Examiner* — Brian J. Sines
(74) *Attorney, Agent, or Firm* — Roche Diagnostics Operations, Inc.

(57) ABSTRACT

A Quality Control (QC) material for performing a QC procedure with respect to at least one detector is introduced. The QC material comprises at least one first QC substance and at least one second QC substance, wherein the first QC substance is interferable with the second QC substance or with the performance and/or lifetime of the detector and wherein the first QC substance is entrapped by carrier particles that prevent the first QC substance to interfere with the second QC substance or with the performance and/or lifetime of the detector. An in-vitro diagnostic system comprising a first detector and a second detector and the QC material is also introduced. An in-vitro diagnostic method comprising performing a QC procedure with respect to a first detector and/or to a second detector comprising providing the QC material is also introduced, as well as a method of manufacturing the QC material.

11 Claims, 6 Drawing Sheets

(51) Int. Cl.
*G01N 33/96* (2006.01)
*G01N 21/47* (2006.01)
*G01N 33/543* (2006.01)

(52) U.S. Cl.
CPC ........... *G01N 33/728* (2013.01); *G01N 33/96* (2013.01); *G01N 33/721* (2013.01); *G01N 2496/15* (2013.01)

(56) References Cited

U.S. PATENT DOCUMENTS

| | | | | |
|---|---|---|---|---|
| 2004/0058458 | A1* | 3/2004 | Anker | G01N 33/58 436/526 |
| 2005/0142567 | A1* | 6/2005 | Su | G01N 21/6428 435/6.11 |
| 2009/0269780 | A1 | 10/2009 | Sorensen et al. | |
| 2012/0104323 | A1 | 5/2012 | Pistorino et al. | |

OTHER PUBLICATIONS

Bagwe, Rahul P. et al., Optimization of Dye-Doped Silica Nanoparticles Prepared Using a Reverse Microemulsion Method, Langmuir, 2004, pp. 8336-8342, vol. 20.

Carbonaro, Carlo Maria et al., High efficient fluorescent stable colloidal sealed dye-doped mesostructured silica nanoparticles, Microporous and Mesoporous Materials, 2016, pp. 432-439, vol. 225.

Gomes, Elis C. C. et al., On the incorporation of Rhodamine B and 2',7'-dichlorofluorescein dyes in silica: Synthesis of fluorescent nanoparticles, Optical Materials, 2014, pp. 1197-1202, vol. 36.

Jing, Lihong et al., Highly Fluorescent CdTe@SiO2 Particles Prepared via Reverse Microemulsion Method, Chemistry of Materials, 2010, pp. 420-427, vol. 22.

Ma, Fei et al., A facile method for hemoglobin encapsulation in silica nanoparticles and application in biosensors, Microporous and Mesoporous Materials, 2012, pp. 106-113, vol. 160.

Si, Di et al., Nanoparticle PEBBLE Sensors for Quantitative Nanomolar Imaging of Intracellular Free Calcium Ions, Analytical Chemistry, 2012, pp. 978-986, vol. 84.

Skirtach, Andre G. et al., Remote Activation of Capsules Containing Ag Nanoparticles and IR Dye by Laser Light, Langmuir, 2004, pp. 6988-6992, vol. 20.

Wang, Lin et al., Dual-Luminophore-Doped Silica Nanoparticles for Multiplexed Signaling, Nano Letters, 2005, pp. 37-43, vol. 5, No. 1.

Zhai, Hong et al., Development of dual-emission ratiometric probe-based on fluorescent silica nanoparticle and CdTe quantum dots for determination of glucose in beverages and human body fluids, Food Chemistry, 2016, pp. 444-452, vol. 204.

* cited by examiner

QUALITY CONTROL MATERIAL, SYSTEM AND METHOD

CROSS-REFERENCE TO RELATED APPLICATIONS

This application claims priority to European Patent Application No. 16191700.0, filed 30 Sep. 2016, the disclosure of which is hereby incorporated by reference in its entirety.

FIELD OF THE DISCLOSURE

The present disclosure refers to a Quality Control (QC) material for in-vitro diagnostics, to a system comprising the QC material, to a method of performing a QC procedure using the QC material, and to a method of manufacturing the QC material.

BACKGROUND

In medicine, a doctor's diagnosis and patient treatment often relies on the measurement of patient sample parameters carried out by in-vitro diagnostic instruments. As the life of patients may depend on the precision and the reliability of such measurements it is important that the instruments perform correctly.

Thus, it is a general requirement for in-vitro diagnostic systems to implement a set of Quality Control (QC) procedures to check that the instruments are working correctly.

One of these procedures is calibration. In most cases calibration is performed using standard solutions, with known concentrations. In this way it is possible to correlate a measured signal to a quantitative result. Calibration should be performed more or less frequently depending on the system and other variable factors that may affect performance. Depending on the circumstances, a two-point or one-point calibration may be performed, eventually with variable frequency.

In addition, between consecutive calibrations, one or more reference samples, also called QC samples, with known values of the parameters of interest are typically also measured, in the same way as patient samples are measured, in order to further check that the calibrated instrument is actually within the specifications or admissible range. Typically, QC samples are supplied in three levels that correspond to different concentration ranges of the parameters.

In some cases, rather than having different calibration solutions and a different QC samples for each different parameter, different standard substances with known concentration can be combined into a single calibration solution or a single QC sample respectively. In this way, the number of calibration solutions and QC samples can be reduced, and also the number of QC procedures can be reduced, since the same QC procedure can be applied to a plurality of parameters at the same time.

One possible problem of this approach is that some QC substances present in the same solution may interfere with each other or if different detectors or measurement principles are used for different parameters respectively, QC substances that are intended for one detector may interfere with the performance and/or lifetime of another detector.

SUMMARY

It is against the above background that the present disclosure provides certain unobvious advantages and advancements over the prior art. In particular, the inventors have recognized a need for improvements in QC materials, systems and methods.

Although the embodiments of the present disclosure are not limited to specific advantages or functionality, it is noted that the present disclosure provides a QC material that solves this interference problem in general. This is achieved by isolation of the interfering substance or substances from other substances in the same solution, as claimed. A method of manufacturing the QC material is also introduced. An in-vitro diagnostic system comprising the QC material and a method of using the QC material are also introduced, which can be employed when using different detectors for different parameters. The present disclosure also provides an increased choice of substances that can be used as standard substances in QC materials, and the possibility to increase the number of different substances in the same QC material. Further, the same QC material may be used for performing a QC procedure on different in-vitro systems by having respective QC substances in the same QC material. Also, although reference is made to a QC material, the same concept of isolating an interfering substance in a complex mixture of substances in order to prevent interferences can be extended to other materials as well, including for example reagents or other fluids used by the in-vitro diagnostic system.

In accordance with one embodiment of the present disclosure, a Quality Control (QC) material for performing a QC procedure with respect to at least one detector is provided, the QC material comprising: at least one first QC substance and at least one second QC substance, wherein the at least one first QC substance is interferable with the at least one second QC substance or with the performance and/or lifetime of the at least one detector, and the at least one first QC substance is entrapped by carrier particles that prevent the at least one first QC substance to interfere with the at least one second QC substance or with the performance and/or lifetime of the at least one detector.

In accordance with another embodiment of the present disclosure, an in-vitro diagnostic system is provided comprising: at least two detectors comprising a first detector and a second detector for detecting at least two respective parameters of a test sample, a QC material in accordance with an embodiment of the present disclosure for performing a QC procedure with respect to the first detector and the second detector, wherein the at least one first QC substance is required for performing the QC procedure with respect to the first detector and the at least one second QC substance is required for performing the QC procedure with respect to the second detector, and wherein the at least one first QC substance is interferable with the performance and/or lifetime of the second detector.

In accordance with yet another embodiment of the present disclosure, an in-vitro diagnostic method is provided comprising: performing a QC procedure with respect to a first detector and/or to a second detector, comprising providing a QC material according to an embodiment of the present disclosure to the first detector and/or to the second detector, wherein the at least one first QC substance entrapped by the carrier particles is required for performing the QC procedure with respect to the first detector and the at least one second QC substance is required for performing the QC procedure with respect to the second detector.

In accordance with still yet another embodiment of the present disclosure, a method of manufacturing a QC material in accordance with an embodiment of the present disclosure is provided, the method comprising mixing the at least one first QC substance with a surfactant and with a silicate or silane derivative for obtaining silica carrier particles that entrap the at least one first QC substance.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

A Quality Control (QC) material for performing a QC procedure with respect to at least one detector is introduced. In particular, the QC material can comprise at least one QC substance that interferes with another QC substance or with the performance and/or lifetime of the at least one detector. More in particular, the QC material can comprise at least one first QC substance and at least one second QC substance, where the at least one first QC substance is interferable with the at least one second QC substance or with the performance and/or lifetime of the at least one detector. In order to prevent that the at least one first QC substance interferes with the at least one second QC substance or with the performance and/or lifetime of the at least one detector the at least one first QC substance is entrapped by carrier particles that isolate the at least one first QC substance in the QC material.

The term "quality control material" or for short "QC material" is herein used to intend either a calibration material, typically a calibration solution, or a quality control sample (QC sample) or both, unless explicitly stated. Analogously, the term "QC procedure" is herein used to intend either a calibration procedure or a check with a quality control sample or both, unless explicitly stated. The QC material can comprise a plurality of QC substances for performing the QC procedure with respect to different parameters respectively.

A "parameter" can be a measurable property of the test sample with diagnostic meaning, such as, for example, turbidity, color, viscosity, hematocrit, coagulation time, and the like, or it can be an analyte present in the test sample, the presence and/or concentration of which has also a diagnostic value.

The term "test sample" refers to a biological material suspected of containing one or more analytes of interest and whose detection, qualitative and/or quantitative, may be associated to a clinical condition. The test sample can be derived from any biological source, such as, for example, a physiological fluid, including blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve, e.g., filtration, centrifugation, distillation, concentration, inactivation of interfering components, and the addition of reagents. A test sample may be used directly as obtained from the source in some cases or following a pretreatment and/or sample preparation workflow to modify the character of the sample, e.g., after adding an internal standard, after being diluted with another solution or after having being mixed with reagents, e.g., to enable carrying out one or more in-vitro diagnostic tests, or for enriching, i.e., (extracting/separating/concentrating) analytes of interest and/or for removing matrix components potentially interfering with the detection of the analyte(s) of interest.

According to an embodiment of the present disclosure, the test sample can be blood or a blood derivative, such as, i.e., plasma or serum. According to certain embodiments, analytes of interest can be gases such as, e.g., $O_2$ and $CO_2$, blood electrolytes such as, e.g., Sodium ($Na^+$), Potassium ($K^+$), Chloride ($Cl^-$), Calcium ($Ca^{++}$), protons ($H^+$) in relation to pH, metabolites such as glucose and lactate, drugs of abuse, therapeutic drugs, hormones, markers, proteins and the like. Other analytes of interest are, e.g., hemoglobin, hemoglobin derivatives such as Deoxygenated hemoglobin, Oxyhemoglobin, Carboxyhemoglobin, Methemoglobin, and bilirubin. According to an embodiment of the present disclosure, a parameter of interest can be hematocrit. The list is however not exhaustive.

A "QC substance" can be an analyte identical to an analyte of interest, the concentration of which is known, or that generates by reaction an analyte identical to an analyte of interest, the concentration of which is known, e.g., $CO_2$ from bicarbonate, or it can be any other equivalent substance of known concentration, which mimics the analyte of interest or that can be otherwise correlated to a certain parameter of interest, e.g., a dye that behaves optically similar to hemoglobin or bilirubin.

Different levels of the QC material with respective different concentrations of QC substances may be prepared for performing a QC procedure.

A "carrier particle" is a chemical vector comprising a three-dimensional body structure that can hold and transport a QC substance by entrapment, e.g., by incorporation into its body or enclosure in its interior. In particular, the carrier particle prevents the QC substance from interacting/interfereing with other substances of the QC material and/or with the at least one detector while possibly still retaining its properties as a QC substance for performing a QC procedure. According to certain embodiments, the carrier particle is a microscopic particle in the micrometer or sub-micrometer range, e.g., a nanoparticle. Carrier particles can be formed under certain conditions by mixing suitable reagents in the presence of the QC substance that is to be entrapped.

According to an embodiment of the present disclosure, the carrier particles are silica or polymeric particles. According to another embodiment of the present disclosure, the carrier particles comprise a silica shell and the at least one first QC substance is enclosed in the silica shell.

According to yet another embodiment of the present disclosure, the first QC substance is enclosed in the silica shell by mixing the first QC substance with a surfactant and with a silicate or silane derivative, such as, for example, tetraethyl orthosilicate or (3-Aminopropyl)triethoxysilane, or an equivalent compound.

According to an embodiment of the present disclosure, the surfactant can be Cetyltrimethylammonium bromide (CTAB) or Triton X-100. However other surfactants may be used.

According to an embodiment of the present disclosure, the first QC substance is a dye that optically simulates one or more analytes of interest or whose optical properties may be correlated to the optical properties of one or more analytes of interest. According to another embodiment of the present disclosure, the first QC substance is a dye that optically simulates hemoglobin or any derivative of hemoglobin, e.g., sulforhodamine B or rhodamine B. According to yet another embodiment of the present disclosure, the first QC substance is a dye that optically simulates bilirubin, e.g., tartrazine. According to still another embodiment of the present disclosure, the first QC substance is a mixture of a dye that optically simulates hemoglobin or any derivative of hemoglobin such as sulforhodamine B and a dye that optically simulates bilirubin such as tartrazine. Any other dyes with similar or correlateable optical properties may however be used.

A method of manufacturing a QC material in accordance with an embodiment of the present disclosure is also introduced. The method can comprise mixing the at least one first QC substance with a surfactant and with a silicate or silane derivative, e.g., with tetraethyl orthosilicate or (3-Aminopropyl)triethoxysilane or equivalent compound, for obtaining silica carrier particles that entrap the at least one first QC substance.

According to another embodiment, the method further comprises isolating the silica carrier particles and adding the carrier particles to a solution comprising the at least one second QC substance in order to form the QC material for performing a QC procedure with respect to the at least one detector.

Isolating the silica carrier particles may be achieved, for example, by centrifugation followed by washing the excess of first QC substance remained in the supernatant. This procedure may be repeated as necessary comprising resuspending the carrier particles. However, other isolating procedures may be used as well, like filtration, evaporation, and the like.

Also, other methods of manufacturing the QC material may be employed, comprising obtaining other types of carrier particles or using different methods of obtaining the carrier particles.

Polymeric carrier particles may be for example obtained as an alternative to silica carrier particles. An exemplary list of polymers that may be used includes Poly (N-isopropylacrylamide) (PNIPAM), Polypyrrole (PPy), Polyallylamine (PAH), Polymethylmethacrylate (PMMA), Polyethyleneimine (PEI), but is not limited thereto.

One possible procedure is based on a layer by layer assembly using electrostatic interactions, e.g., as disclosed in Langmuir 2004, 20, 6988-6992, which is hereby incorporated herein be reference.

Other methods like water/oil/water emulsion can be used to obtain polymeric capsules as well. In that case, a solvent with opposite polarity from the polymer is typically used together with a surfactant to stabilize the emulsion.

An in-vitro diagnostic system in accordance with an embodiment of the present disclosure is also introduced, which system comprises at least two detectors, in particular at least a first detector and a second detector for detecting at least two respective parameters of a test sample. The in-vitro diagnostic system can further comprise the above QC material for performing a QC procedure with respect to the first detector and the second detector, where the at least one first QC substance is required for performing the QC procedure with respect to the first detector but is interferable with the performance and/or lifetime of the second detector, and the at least one second QC substance is required for performing the QC procedure with respect to the second detector. However, as the at least one first QC substance is entrapped by the carrier particles it is thereby prevented from interfering with the performance and/or lifetime of the second detector.

An "in-vitro diagnostic system" is a laboratory automated system dedicated to the analysis of samples for in-vitro diagnostics and making use of QC materials. The in-vitro diagnostic system may have different configurations according to the need and/or according to the desired laboratory workflow. The in-vitro diagnostic system can comprise one or more analytical apparatuses, comprising at least one detector, designed to execute respective workflows that are optimized for one or more certain types of analysis, and to detect certain types of parameters, e.g., gases, electrolytes, metabolites, clinical chemistry analytes, immunochemistry analytes, coagulation parameters, hematology parameters, etc. Thus the in-vitro diagnostic system may comprise one analytical apparatus or a combination of any of such analytical apparatuses with respective workflows and respective detectors, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The in-vitro diagnostic system can comprise functional units such as liquid handling units for pipetting and/or pumping and/or mixing of samples and/or reagents and/or system fluids, and also functional units for sorting, storing, transporting, identifying, separating, and/or detecting.

According to an embodiment of the present disclosure, the in-vitro diagnostic system can comprise an analytical apparatus with at least a first detector and a second detector and which uses one or more QC materials.

According to another embodiment. the in-vitro diagnostic system can comprise at least two analytical apparatuses with at least a first detector and a second detector, respectively, and which uses one or more QC materials.

According to yet another embodiment of the present disclosure, the first detector can comprise an optical unit for optically detecting at least one analyte of interest. The first detector is however not limited to optical detectors.

According to still another embodiment of the present disclosure, the optical unit can be an oximetry unit for photometrically detecting any one or more of hemoglobin, including any derivatives of hemoglobin, and bilirubin. In particular, the oximetry unit can comprise at least one light source, at least one optical sensor, e.g., a photodiode array, a sample cuvette arranged between the light source and the optical sensor, and optical elements such as lenses, apertures, possibly mirror(s), possibly filter(s), possibly a grating monochromator, a polychromator or prism, for guiding light from the light source to a test sample in the cuvette and from the test sample to the at least one optical sensor. Absorbance and, in particular, an absorbance spectrum and/or scattering can be measured. Absorbance can also be measured directly in a flow path.

According to yet still another embodiment of the present disclosure, the at least one second detector can comprise a flow-through sensoric path for detecting any one or more of a gas, an electrolyte, and/or a metabolite.

The flow-through sensoric path may comprise a sensor for each parameter, and may be embodied in a replaceable cartridge-like structure comprising a plurality of sensors. In alternative, the in-vitro diagnostic system may comprise a plurality of second detectors, each having a sensoric path comprising a sensor dedicated to one parameter, and which may also be replaceable or not. According to an embodiment the sensor can be a thick-film sensor. A test sample may thus flow into the one or more sensoric paths and different parameters may be determined by respective sensors.

According to certain embodiments of the present disclosure, the at least one second detector can comprise any one or more of a PO2 sensor, a PCO2 sensor, a pH sensor, one or more ion selective electrode (ISE) sensors for determining electrolyte values such as Na+, K+, Ca2+ and Cl−, and/or one or more metabolite sensors for determining parameters such as lactate and glucose.

A PO2 sensor typically functions according to the Clark measurement principle. This means that oxygen diffuses through a membrane to a gold multi-wire system with negative electric potential inside of the sensor. The oxygen is reduced there, which generates an electric current that is proportional to the oxygen contained in the sample. This current can be measured amperometrically.

A PCO2 sensor typically is a Severinghouse-type sensor. This means that CO2 diffuses through a membrane similar to the oxygen sensor. In the sensor, the CO2 concentration changes and causes a change of the pH value, which can be measured potentiometrically.

A pH sensor typically comprises a pH-sensitive membrane. Depending on the pH value of the test sample, electric potential is generated at the boundary layer between the membrane and the sample. This potential can be measured potentiometrically by a reference sensor.

Na+, K+, Ca2+ and Cl− ISE sensors typically work according to the potentiometric measuring principle. They differ only by different membrane materials that enable sensitivity for the respective electrolytes.

The glucose sensor typically makes use of glucose oxidase enzyme, by which glucose is oxidized into gluconolactone with oxygen from the air. The H2O2 that is formed in this process can be determined amperometrically by a manganese dioxide/carbon electrode. Since the sensor restores the oxygen that is needed for oxidation of glucose in the enzymatic reaction, the glucose value can be measured independently of the oxygen concentration in the test sample.

The lactate sensor typically makes use of lactate oxidase enzyme, by which lactate is oxidized into pyruvate with oxygen from the air. The H2O2 that is formed in this process can be determined amperometrically in a manner similar to the glucose sensor.

According to certain embodiments of the present disclosure the at least one second detector can comprise additional or different sensors, eventually based on a different principle, e.g., the conductometric principle.

According to an embodiment of the present disclosure, the second detector comprises at least one sensor, the performance and/or lifetime of which is affected by the at least one first QC substance. According to an embodiment the affected sensor is a sensor comprising a membrane that can interact, e.g., by sorption, including adsorbion and/or absorbtion, with the at least one first QC substance, for example an ion selective electrode sensor. By adsorbing/absorbing into the membrane, the first QC substance interferes with the intended function of the membrane. In particular, it competes with the parameter, e.g., with the electrolyte that the sensor is intended to measure, affecting the membrane permeability and selectivity to that electrolyte.

According to one embodiment, if the first QC substance is a negatively charged substance, like for example sulphorodamine B or tartrazin, it can interfere with the chloride ISE sensor comprising a Cl− selective membrane. Analogously, if the first QC substance is a positively charged substance it can interfere with any other of the other sensors selective to positively charged parameters.

As QC procedures are repeated and more and more of the first QC substance becomes eventually adsorbed/absorbed, the performance of the sensor can become worse with time and eventually shorten its lifetime. Moreover, if the sensor is integrated into a sensor cartridge with other sensors, then the entire cartridge may need to be replaced. This results in increased costs and increased downtime of the in-vitro diagnostic system.

By entrapping any interfering QC substance into carrier particles the performance and the regular lifetime of the at least one second detector is therefore preserved.

One possible side effect associated with the use of carrier particles can be an enhanced scattering effect. If the detector subject to the QC procedure is based on a non-optical principle, e.g., on the amperometric, potentiometric or conductometric measurement principle, and the QC substance required for performing the QC procedure by the detector is not the one entrapped by the carrier particles, scattering does not play any role. This is the case for the second detector according to certain embodiments of the present disclosure. Scattering may be generated and may interfere with the QC procedure if the detector subject to the QC procedure is an optical detector and if the QC procedure is based on optical detection of a QC substance. This may be the case for the first detector, according to certain embodiments. Depending on the particular optical setup, light scattering may be taken into account when measuring absorbance and is not necessarily a negative side effect. In other circumstances however, it is desirable to minimize any scattering effects.

According to an embodiment, the in-vitro diagnostic system can comprise a disruptive device associated with the first detector for disrupting the carrier particles and releasing the at least one first QC substance.

Regardless of any scattering effect, depending on the chemical structure of the at least one first QC substance, it may be desirable to disrupt the carrier particles at the first detector where the released first QC substance(s) cannot interfere with the performance and/or lifetime of the second detector. By this, it can be ensured that the at least one first QC substance behaves as in any other QC material comprising that same QC substance without being entrapped by carrier particles. Thereby any possible alteration of the QC procedure is also avoided, e.g., a possible shift in the absorbance spectrum or of the intensity.

According to an embodiment, the disruptive device can be an ultrasound generator, e.g., comprising a piezo element, for generating and transferring ultrasound waves to the QC material in the optical cuvette or before entering the optical cuvette. Other types of disruptive devices may however be used such as, for example, based on mechanical stressing, temperature or ablative decomposition.

According to an embodiment, the disruptive device can also be a hemolizer used to disrupt cells, in particular red blood cells in a blood sample and to release hemoglobin from the cells, as the cells may also generate scattering.

An in-vitro diagnostic method in accordance with an embodiment of the present disclosure is also introduced. The method comprises performing a QC procedure with respect to a first detector and/or to a second detector. The method further comprises providing a QC material according to any of the mentioned embodiments to the first detector and/or to the second detector, where the at least one first QC substance entrapped by the carrier particles is required for performing the QC procedure with respect to the first detector and the at least one second QC substance is required for performing the QC procedure with respect to the second detector.

The first detector and the second detector do not have to be arranged necessarily in the same in-vitro diagnostic system. This method refers to the use of the same QC material for performing a QC procedure with respect to different detectors regardless of their arrangement in space and regardless of the time of use.

According to an embodiment, performing the QC procedure with respect to the first detector can comprise disrupting the carrier particles for releasing the at least one first QC substance, where the released at least one first QC substance at the first detector cannot interfere with the performance and/or lifetime of the second detector.

Other and further objects, features and advantages will appear from the following description of exemplary embodiments and accompanying drawings, which serve to explain the principles more in detail.

Figure 1:
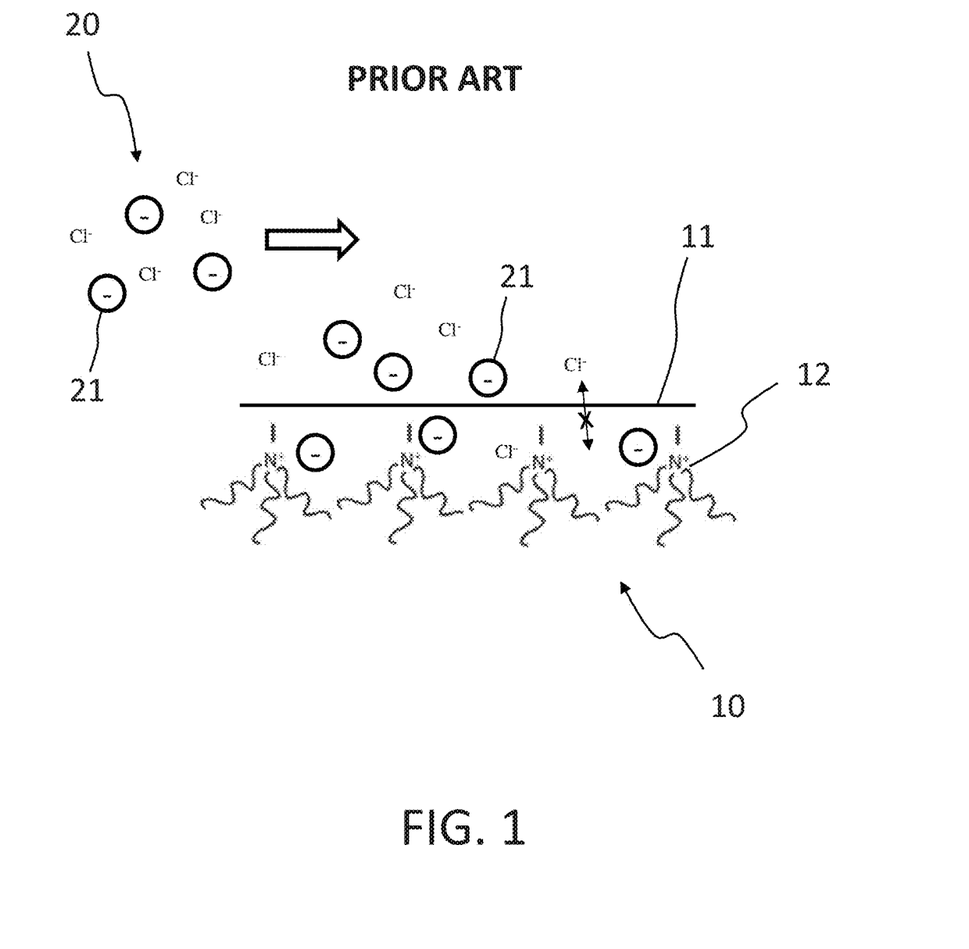
FIG. 1 schematically shows a possible problem encountered in the prior art.

FIG. 1 schematically shows a membrane 11 used in an ion selective electrode (ISE) sensor 10, in this case a chloride (Cr) selective membrane 11.

This chloride selective membrane 11 comprises a quaternary ammonium salt 12, tridodecylmethylammoniumchloride (TDMAC), which acts as a positively charged ion-exchanger. The membrane 11 can be formed by embedding the quaternary ammonium salt 12 for example in polyvinylchloride (PVC) or in an epoxy resin, e.g., Araldit composed of mainly diglycidyl end capped bisphenol A (DGEBPA) and polypropylene glycol-diglycidyl ether (PPG-DGE), which is hardened and crosslinked with an aliphatic tetraamine. The chloride selective membrane 11 is selective for chloride but not specific for chloride. In general, selectivity decreases with the increased hydrophilicity of the ion and increases with increased hydrophobicity of the ion. For example, when analyzing a test sample from a patient taking aspirin, salicylate, which is more hydrophobic than Cl⁻, can produce a positive interference. Analogously when using a prior art QC material 20 comprising a at least one first QC substance 21, for performing a QC procedure with respect to another detector (not shown in FIG. 1) together with at least one second QC substance, in this case Cl⁻ for performing a QC procedure with respect to the chloride sensor 10 respectively, the first QC substance 21 may compete with the second QC substance Cl⁻ in the ion exchange process with the membrane 11, especially if the first QC substance 21 is more hydrophobic than Cl⁻, e.g., if the first QC substance 21 is a dye such as sulphorodamine B or tartrazin or both. Eventually more and more of the first QC substance 21 is adsorbed/absorbed by the membrane 11 and it cannot be replaced by chloride. This is an example of how a QC substance can interfere with the performance and/or lifetime of a detector.

Figure 2:
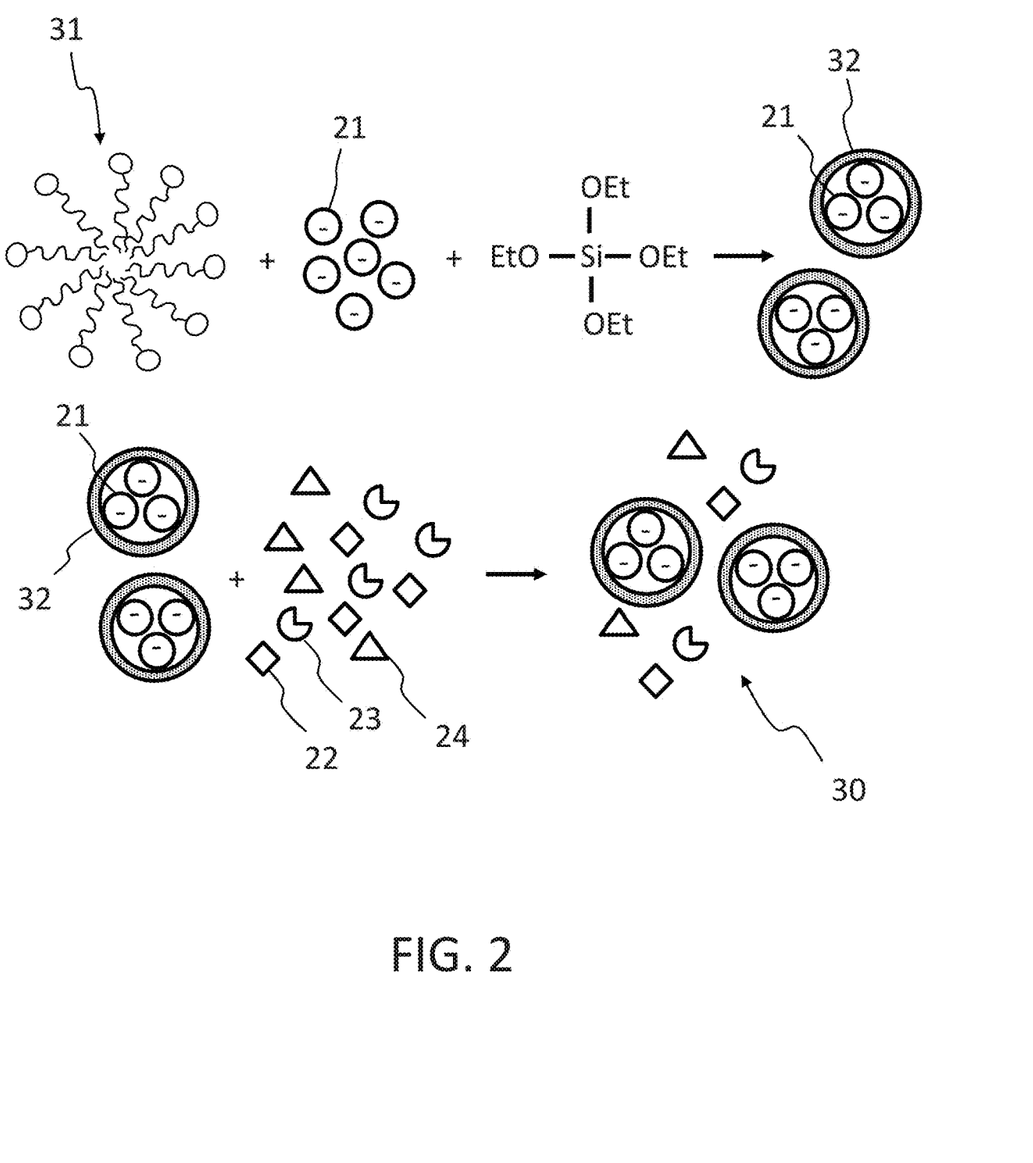
FIG. 2 schematically shows a QC material and a method of manufacturing the QC material in accordance with one or more embodiments of the present disclosure.

FIG. 2 schematically shows a new QC material 30 and a method of manufacturing it. The method comprises mixing at least one first QC substance 21 that is interferable with a second QC substance or with the performance and/or lifetime of at least one detector, with a surfactant 31 (represented as a micelle in FIG. 2) and with a silicate or silane derivative, tetraethyl orthosilicate (TEOS) in this case, for obtaining carrier particles, in this case silica capsules 32 that entrap by enclosure the at least one first QC substance 21 in a silica shell.

Different methods of manufacturing silica carrier particles entrapping different types of substances, including dyes such as Rhodamine B, are known in the art, e.g., as disclosed by Gomes et al. (2014), Optical Materials, 36, 1197-1202. However, the carrier particles obtained have generally different applications.

Following the method reported by Gomes et al, silica capsules enclosing for example sulforhodamine B can be obtained. In particular, Cetyltrimethylammonium bromide (CTAB) is added as surfactant to a solution of $NH_4OH$. The mixture is stirred until the surfactant is dissolved. Afterwards, Sulforhodamine B is added to the solution and stirred until also dissolved. Thereafter a solution of TEOS in ethanol is added and left reacting at room temperature under stirring thereby obtaining the silica capsules. The silica capsules can be recovered (isolated) by centrifugation and excess of dye can be removed by repeated cycles of washing/resuspending/centrifuging. More specific conditions can be found for example in the referenced article.

The method of manufacturing the new QC material 30 further comprises isolating the silica capsules 32 and adding the silica capsules 32, in the desired amount, to a solution comprising at least one second QC substance 22, 23, 24, in order to form the QC material 30 comprising the at least one QC substance 21 enclosed in the silica capsules 32 in the desired concentration, for performing a QC procedure with respect to the at least one detector requiring any of the first and second QC substances. So, when it comes to a detector where the first QC substance 21 would interfere with its performance and/or lifetime, it is prevented from interfering. Also, it is prevented from interfering with any other QC substance in the same QC material 30.

Figure 3:
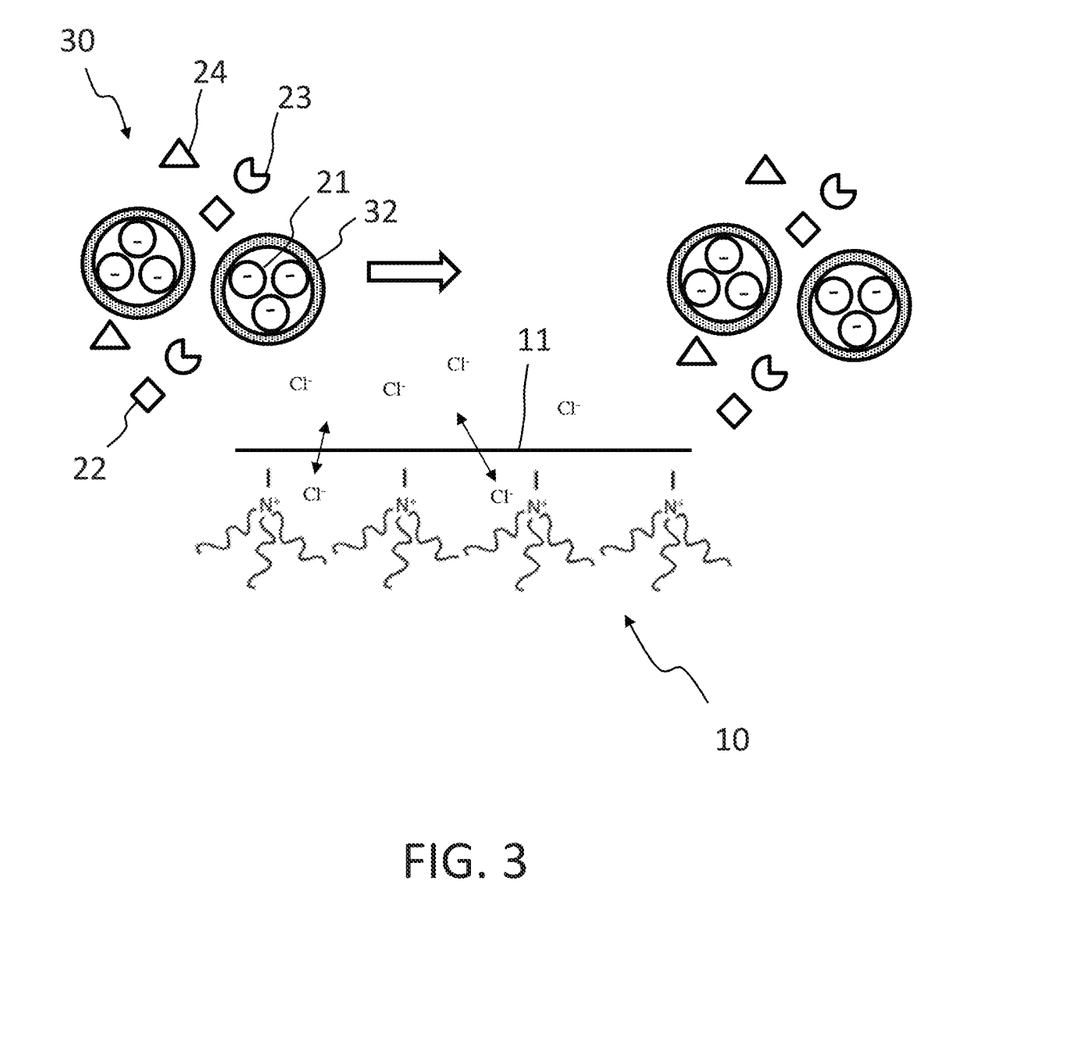
FIG. 3 schematically shows how the problem embodied in FIG. 1 can be solved by using the QC material of FIG. 2.

FIG. 3 schematically shows how the interference problem illustrated in connection with FIG. 1 can be prevented by using the new QC material 30. The QC material 30 includes, for continued reference, also the QC substance Cl⁻ along other second QC substances 22, 23, 24. In this case, as the first QC substance 21 is enclosed in the silica capsules 32, it is prevented to adsorb/absorb into the membrane 11 and to compete in the ion exchange process with the second QC substance Cl⁻, which is the QC substance for performing a QC procedure with respect to the chloride sensor 10. The first QC substance 21 therefore cannot interfere with the performance and lifetime of the chloride sensor 10.

Figure 4:
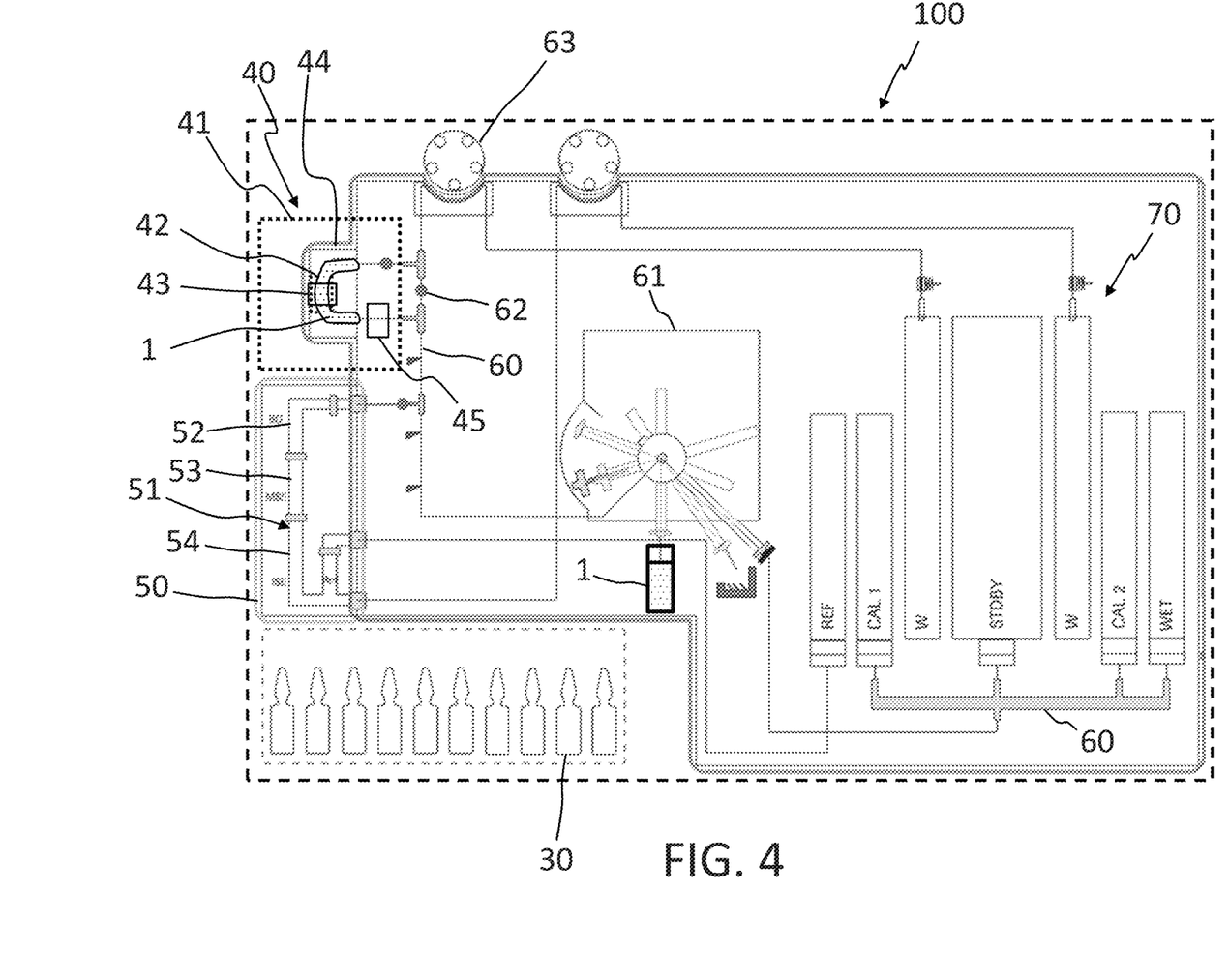
FIG. 4 shows an example of an in-vitro diagnostic system in accordance with an embodiment of the present disclosure.

FIG. 4 shows schematically an example of an in-vitro diagnostic system 100. The in-vitro diagnostic system 100 comprises a first detector 40 and a second detector 50 for detecting respective parameters of a test sample 1.

The first detector 40 comprises an optical unit 41 and in particular an oximetry unit for photometrically detecting any one or more of hemoglobin, including derivatives of hemoglobin, and bilirubin. In particular, the oximetry unit 41 comprises a light source 42, an optical sensor 43 such as a photodiode array, a sample cuvette 44 arranged between the light source 42 and the optical sensor 43 and optical elements such as lenses and a polychromator (not shown), for guiding light from the light source 42 to a test sample 1 in the cuvette 44 and from the test sample 1 to the optical sensor 43 for measuring an absorbance spectrum.

The second detector 50 is embodied as a plug-in cartridge comprising a flow-through sensoric path 51, comprising a gas sensoric zone 52 comprising a $PO_2$ sensor, a $PCO_2$ sensor and a pH sensor, a metabolite sensoric zone 53, comprising a glucose sensor and a lactate sensor, and an electrolyte sensoric zone 54, comprising ISE sensors for detecting respectively $Na^+$, $K^+$, $Ca^{2+}$, and the chloride ISE sensor 10 seen in connection to FIG. 1.

The in-vitro diagnostic system 100 further comprises fluidic lines 60, a fluid injector 61, valves 62 and pumps 63 for moving fluids through the fluidic lines 60 and in particular in and out of the cuvette 44 of the first detector 40 and/or through the sensoric path 51 of the second detector 50, where respective test sample parameters can be determined.

The in-vitro diagnostic system 100 further comprises a fluid package 70 comprising fluid reservoirs, including a reference solution (REF) for the second detector 50, a first calibration material (Cal 1), a second calibration material (Cal 2), a standby solution (STDBY), a wetting fluid (WET) and two waste containers (W). The wetting fluid (WET) is used every time a new cartridge 50 is plugged for conditioning the new cartridge 50.

The $Na^+$, $K^+$, $Ca^{2+}$, $Cl^-$, pH and $CO_2$ parameters are calibrated using the standby (STDBY) and CAL 2 solutions, which contain a defined quantity of electrolytes and acidic or alkaline components of a pH buffer system. By ensuring airtight access to the calibration solutions, the $CO_2$ content can be kept steady and then used as a basis for calibration.

The CAL 2 solution contains a very low concentration of oxygen and thus is used to calibrate the low calibration point in a two-point calibration. The high calibration point is calibrated using the standby solution. The oxygen concentration of the standby solution corresponds to that of the ambient air.

For the glucose/lactate sensors, due to the non-linear nature of the calibration curve, three calibration points are determined. The standby, CAL 1 and CAL 2 solutions are used for this purpose.

Calibrating the oximetry unit 41 requires wavelength calibration of the polychromator and layer thickness calibration of the cuvette 44. For this purpose, the optical unit 41 comprises a second light source (not shown), which is a neon lamp. The neon lamp is a gas discharge light, which emits only certain defined wavelengths. The peaks in the neon emission spectrum are used to calibrate the wavelength scale. Layer thickness of the cuvette 44 is calibrated using the CAL 2 solution which contains a dye for this purpose.

The standby solution (STDBY) is also used for rinsing the fluidic lines 60, the flow-through path 51 and the cuvette 44.

The in-vitro diagnostic system 100 further comprises QC materials 30 for performing other QC procedures with respect to the first detector 40 and the second detector 50 and in particular quality control samples, supplied in three levels of respective concentration ranges for each parameter. In particular, the QC materials 30 comprise QC substances in different concentrations for different levels, which are required for performing the QC procedure with respect to both the first detector 40 and the second detector 50. Among the QC substances there are two QC substances, sulphorodamine B and tartrazin, which are required for performing the QC procedure with respect to both the first detector 40 that are interferable with the performance and lifetime of the second detector 50, and in particular with that of the chloride ISE sensor in the electrolyte sensoric zone 54. For this reason, the two interferable QC substances are enclosed in carrier particles as seen, e.g., in connection to FIGS. 2 and 3, and are thereby prevented from interfering with the performance and/or lifetime of the second detector 50.

The in-vitro diagnostic system 100 further comprises a disruptive device 45 associated with the first detector 40 for disrupting the carrier particles and releasing the enclosed QC substances. The disruptive device 45 is an ultrasound generator that transfers ultrasound waves to the QC material 30 in the fluidic lines 60 before entering the optical cuvette 44. The disruptive device 45 is also a hemolizer used to disrupt cells, in particular red blood cells in a blood sample and to release hemoglobin from the cells.

Whereas the CAL 1 and STDBY solutions comprise mixtures of QC substances for performing calibration procedures and hence QC procedures, they do not contain in this specific example any QC substances that interfere with other QC substances or with the performance and lifetime of any of the first and first detectors 40, 50. Therefore, they do not contain any QC substance enclosed in carrier particles, although in other embodiments, the use of encapsulation of QC substances in carrier particles can be used for these or other solutions with similar purpose as well. According to an embodiment the dye in the CAL 2 solution that is used for calibrating the cuvette 44 in the first detector 40 is also entrapped by carrier particles so that when CAL 2 is used for calibrating the second detector 50, the dye cannot interfere with the performance and/or lifetime of the detector 50. Thus, according to an embodiment the calibration material CAL 2 is another example of QC material.

Figure 5:
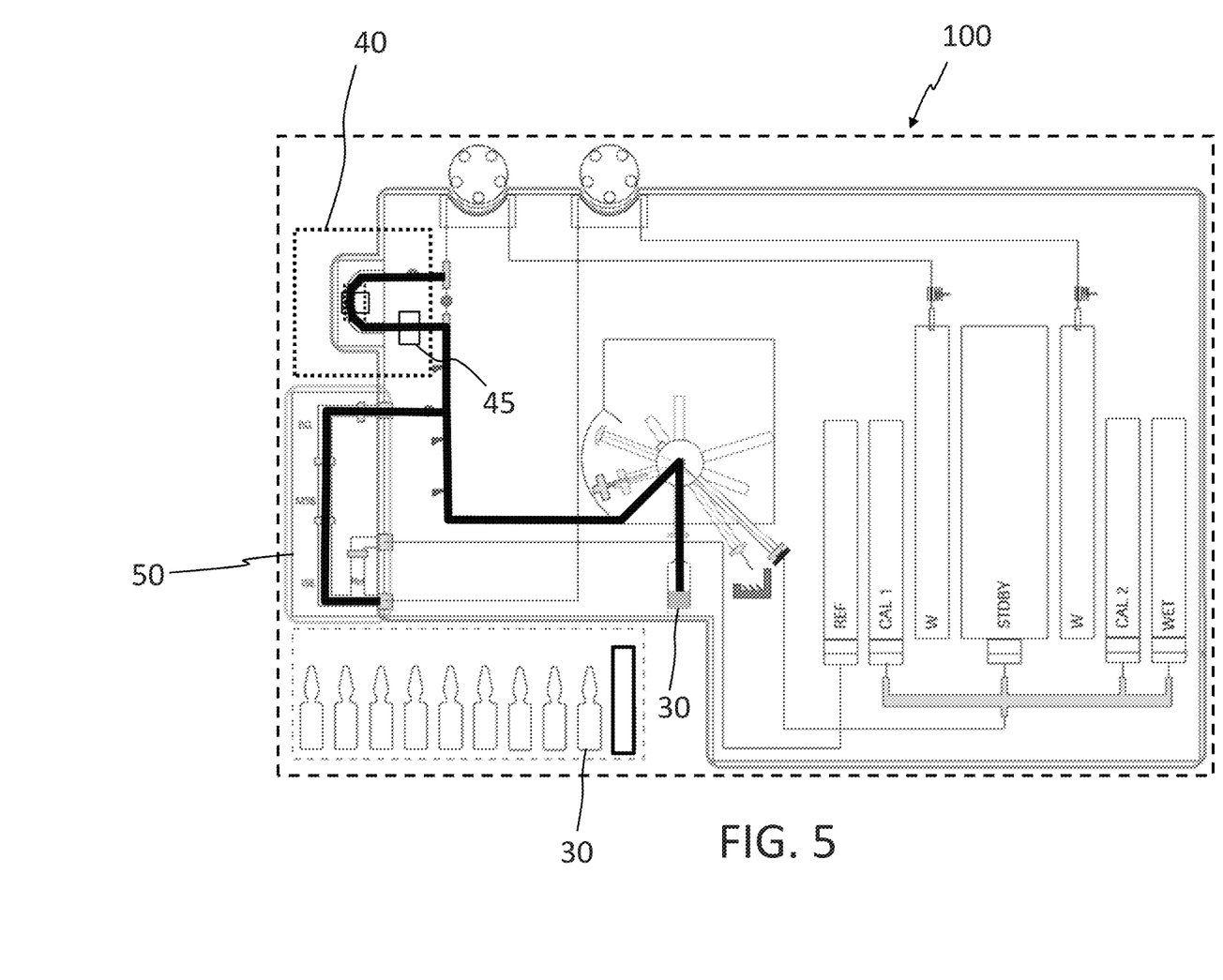
FIG. 5 shows schematically an in-vitro diagnostic method comprising a QC procedure in accordance with an embodiment of the present disclosure.

FIG. 5 shows schematically an in-vitro diagnostic method comprising a QC procedure in connection to the in-vitro diagnostic system 100 of FIG. 4 and using a QC material 30 as discussed in connection to FIGS. 2 and 4.

The method comprises performing a QC procedure with respect to the first detector 40 and to the second detector 50. The method further comprises providing a QC material 30 to the first detector 40 and to the second detector 50, the QC material 30 comprising first QC substances that are required for performing the QC procedure with respect to the first detector 40 and second QC substances required for performing the QC procedure with respect to the second detector 50, where the first QC substances are entrapped by carrier particles in order to prevent the first QC substances to interfere with the performance and/or lifetime of the second detector 50.

Although in FIG. 5 the QC material 30 is being provided to both the first detector 40 and the second detector 50 at the same time, it can be provided to any of the first detector 40 or the second detector 50 independently from each other at any time, according to, e.g., a programmed schedule or on request.

Figure 6:
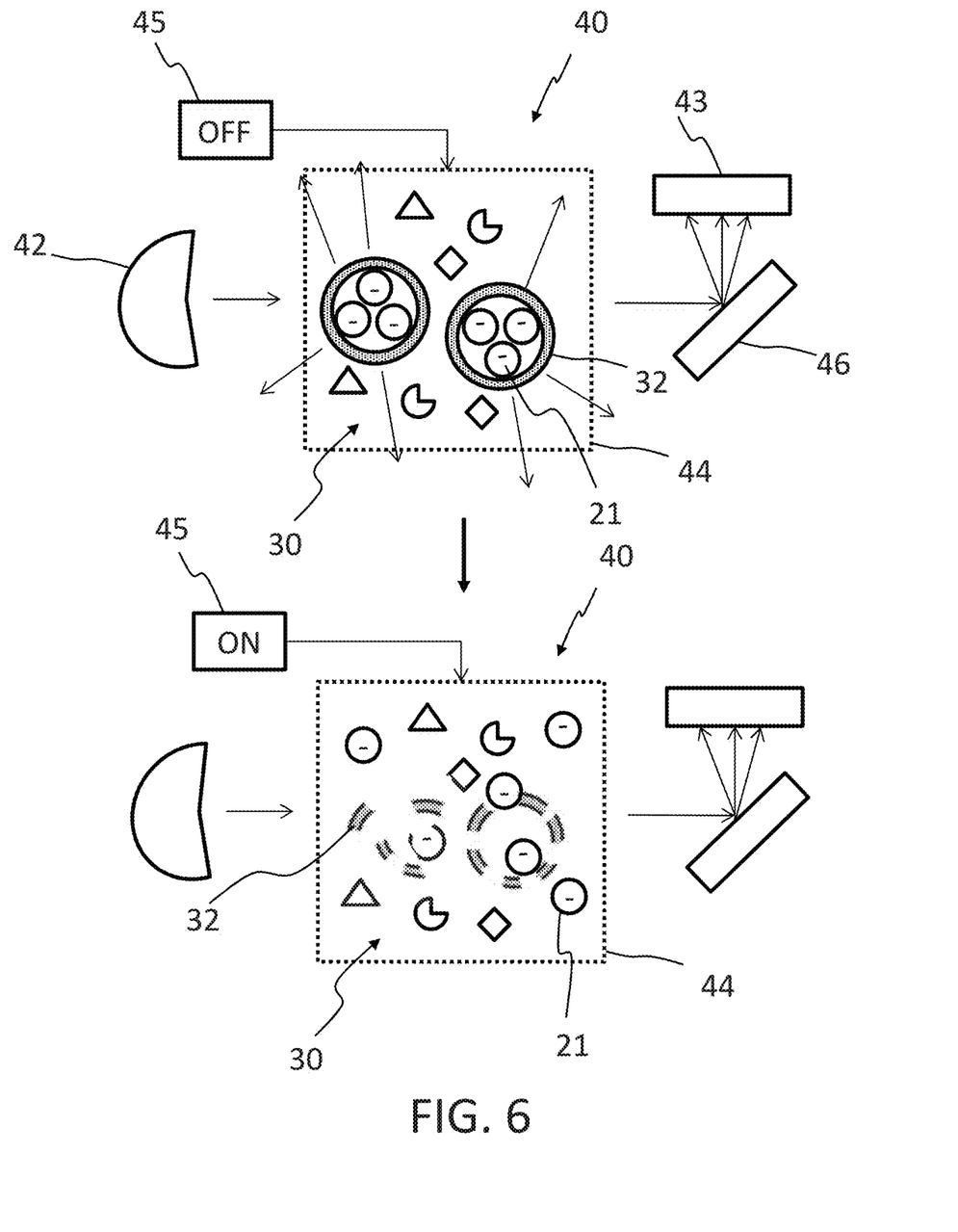
FIG. 6 shows schematically a further embodiment of the in-vitro diagnostic method in accordance with an embodiment of the present disclosure.

With combined reference to FIG. 6, which schematically shows some elements of the first detector 40, including the light source 42, the optical sensor 43, a polychromator 46, the sample cuvette 44, and the disruptive device 45, it can be seen that the carrier particles 32 of the QC material 30 can generate some light scattering. According to an embodiment, the QC procedure further comprises disrupting the carrier particles 32 with the disruptive device 45 for disrupting the carrier particles 32 and releasing the first QC substances 21 at the first detector 40 only, where the released first QC substances 21 at the first detector 40 cannot interfere with the performance and/or lifetime of the second detector 50. In this way any light scattering effect can be prevented or minimized.

Modifications and variations of the disclosed embodiments are certainly possible in light of the above description. It is therefore to be understood, that within the scope of the appended claims, the embodiments may be practiced otherwise than as specifically devised in the above examples.

It is noted that terms like "preferably," "commonly" and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

For purposes of describing and defining the subject matter of the present disclosure it is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. An in-vitro diagnostic system comprising:
    at least two detectors comprising a first detector and a second detector for detecting at least two respective parameters of a test sample, wherein the at least two detectors are different types of detectors,
    a Quality Control (QC) material for performing a QC procedure with respect to the first detector and the second detector, the QC material comprising at least one first QC substance and at least one second QC substance, wherein the at least one first QC substance is required for performing the QC procedure with respect to the first detector and the at least one second QC substance is required for performing the QC procedure with respect to the second detector, and wherein the at least one first QC substance is interferable with the performance and/or lifetime of the second detector, wherein
    the at least one first QC substance is a dye or a mixture of dyes that optically simulate one or more analytes of interest,
    the at least one second QC substance is any one or more of a gas, an electrolyte, and/or a metabolite, and
    the at least one first QC substance is entrapped by carrier particles that prevent the at least one first QC substance to interfere with the at least one second QC substance or with the performance and/or lifetime of the second detector.

2. The in-vitro diagnostic system according to claim 1, wherein the first detector comprises an optical unit for optically detecting at least one analyte of interest.

3. The in-vitro diagnostic system according to claim 2, wherein the optical unit is an oximetry unit for photometrically detecting any one or more of hemoglobin, including any derivatives of hemoglobin.

4. The in-vitro diagnostic system according to claim 2, wherein the optical unit is an oximetry unit for photometrically detecting bilirubin.

5. The in-vitro diagnostic system according to claim 1, wherein the second detector comprises a flow-through sensoric path for detecting any one or more of a gas, an electrolyte, and/or a metabolite.

6. The in-vitro diagnostic system according to claim 5, wherein the second detector comprises at least one sensor that can interact with the at least one first QC substance.

7. The in-vitro diagnostic system according to claim 1, further comprising a disruptive device associated with the first detector for disrupting the carrier particles and releasing the at least one first QC substance.

8. The in-vitro diagnostic system according to claim 7, wherein the disruptive device is an ultrasound generator.

9. The in-vitro diagnostic system according to claim 1, wherein the second detector is based on an amperometric, potentiometric or conductometric measurement principle.

10. The in-vitro diagnostic system according to claim 1, wherein the carrier particles are silica or polymeric particles.

11. The in-vitro diagnostic system according to claim 1, wherein the carrier particles comprise a silica shell and the at least one first QC substance is enclosed in the silica shell by mixing the at least one first QC substance with a surfactant and a silicate or silane derivative.

* * * * *